(12) United States Patent
Fleury et al.

(10) Patent No.: US 8,024,960 B2
(45) Date of Patent: Sep. 27, 2011

(54) METHOD AND DEVICE FOR EVALUATING FLOW PARAMETERS AND ELECTRIC PARAMETERS OF POROUS MEDIUM

(75) Inventors: Marc Fleury, La Celle-Saint-Cloud (FR); Philippe Poulain, Carrières-Sous-Poissy (FR); Patrick Egermann, Rueil-Malmaison (FR)

(73) Assignee: Institut Francais du Petrole, Cedex (FR)

( * ) Notice: Subject to any disclaimer, the term of this patent is extended or adjusted under 35 U.S.C. 154(b) by 782 days.

(21) Appl. No.: 11/912,512

(22) PCT Filed: Apr. 24, 2006

(86) PCT No.: PCT/FR2006/000911
§ 371 (c)(1),
(2), (4) Date: Jun. 6, 2008

(87) PCT Pub. No.: WO2006/114509
PCT Pub. Date: Nov. 2, 2006

(65) Prior Publication Data
US 2009/0126462 A1    May 21, 2009

(30) Foreign Application Priority Data

Apr. 26, 2005  (FR) .................................... 05 04272

(51) Int. Cl.
*G01N 15/08* (2006.01)
*G01V 3/00* (2006.01)
(52) U.S. Cl. ........................................... 73/38; 324/376
(58) Field of Classification Search ....... 73/38; 324/376
See application file for complete search history.

(56) References Cited

U.S. PATENT DOCUMENTS

| 4,679,422 | A | * | 7/1987 | Rubin et al. | 73/38 |
| 5,105,154 | A | | 4/1992 | Givens et al. | |
| 5,209,104 | A | * | 5/1993 | Collins et al. | 73/38 |
| 5,297,420 | A | * | 3/1994 | Gilliland et al. | 73/38 |
| 5,363,692 | A | * | 11/1994 | Lafargue et al. | 73/38 |
| 5,463,894 | A | | 11/1995 | Fleury et al. | |
| 5,493,226 | A | * | 2/1996 | Honarpour et al. | 324/376 |
| 5,610,524 | A | | 3/1997 | Longeron et al. | |
| 5,679,885 | A | * | 10/1997 | Lenormand et al. | 73/38 |
| 5,698,772 | A | * | 12/1997 | Deruyter et al. | 73/38 |

FOREIGN PATENT DOCUMENTS

| EP | 0 603 040 A1 | 6/1994 |
| GB | 2 280 512 A | 2/1995 |
| GB | 2322942 A * | 9/1998 |

* cited by examiner

*Primary Examiner* — Daniel Larkin
(74) *Attorney, Agent, or Firm* — Antonelli, Terry, Stout & Kraus, LLP.

(57) ABSTRACT

A method and device is disclosed for evaluating simultaneously, and with the same equipment, the electric resistivity and flow parameters of a porous medium, from experimental measurements obtained from at least one multi-flow type displacement experiment which has application in oil reservoir development. The method continuously measures as a function of time the differential pressure between two ends of a sample, the electric resistivity of the sample and, for each stabilization step, at least two values of a displaced fluid production volume are also measured. A continuous curve of the displaced fluid production volume, from which flow parameters are estimated by means of a numerical flow simulator, is then deduced therefrom.

13 Claims, 8 Drawing Sheets

METHOD AND DEVICE FOR EVALUATING FLOW PARAMETERS AND ELECTRIC PARAMETERS OF POROUS MEDIUM

BACKGROUND OF THE INVENTION

1. Field of the Invention

The present invention relates to a method and to a device for evaluating flow parameters and electric parameters of a porous medium, with the same equipment, the same experiment and from the same rock sample taken from this medium. It can be, for example, rocks from an underground fluid reservoir zone (hydrocarbon reservoir, aquifer, etc.). More particularly, the invention relates to the measurement of the relative permeability and of electrical parameters (resistivity) of a porous medium by subjecting a sample of this medium successively to one or more drainage or imbibition stages.

2. Description of the Prior Art

Starting production of an oil-bearing field therefore requires precise study of the hydrocarbon recovery conditions. It determines, on the one hand, the amount of hydrocarbon in place and, on the other hand, the multiphase flow parameters in the rock that makes up the reservoir, notably during water or oil injection stages.

The rocks that make up a reservoir can be of different natures in terms of petrophysical properties and it is commonplace to divide them into groups referred to as "rock types" so as to work on samples belonging to the same family or rock type. For each family, it is thus necessary to carry out all of the petrophysical measurements to parametrize the simulator, calculate the amounts in place, etc., because these various parameters vary from family to family. For a given rock type, it is thus commonplace to carefully select several samples, one being used for determination of the capillary pressure curves (Pc), the other for the relative permeability curves (krs), another for the resistivity curves, etc.

Determination of multiphase flow parameters such as the relative permeability and the capillary pressure also is a major stage within the context of oil production, whether in the reservoir evaluation stage or when starting production. The relative permeabilities (krs) are used in numerical simulators to describe multiphase flows in the rock, in particular when water or gas is injected to maintain the pressure and recover more oil. These curves typically allow controlling the production profile in reservoirs. Laboratory experiments carried out under reservoir pressure and temperature conditions are commonly conducted to determine these parameters in a representative manner. In particular, the relative permeabilities are conventionally obtained by means of displacement experiments such as those described in French Patent 2,708,742 and corresponding U.S. Pat. No. 5,679,885. These multi-flow displacement experiments inject a fluid (referred to as injected fluid) into a rock sample initially saturated with predominantly another fluid (referred to as displaced fluid). The injected fluid then drains part of the saturating fluid out of the sample. The amount of displaced fluid thus produced by the sample is measured in a volume. This volume is referred to as displaced fluid production volume. As injection is continued, the amount of displaced fluid produced increases, that is the production volume of displaced fluid increases. Stabilization of this volume is reached thereafter, that is the volume no longer increases. This corresponds to a stop in the production of the fluid displaced out of the sample. The injection rate is then increased to drain part of the saturating fluid still in place in the sample, until a new stabilization step is reached. The injection rate is thus increased several times (after each stabilization step) and, for each one of these steps, the evolution of the following parameters, which make up the experimental data, is measured: differential pressure, for one of the fluids, on either side of the sample, denoted by $\Delta P^j(t)$, displaced fluid production volume, denoted by $V(t_i)$, local saturation for one of the two fluids (injected or displaced fluid) and for each injection stage, denoted by $S(t_1), S(t_2), \ldots$ . The injected fluid can be, for example, water, and the displaced fluid can be oil. The relative permeabilities are then obtained after a stage of analytical interpretation of the experimental data, as well as a numerical stage using a flow simulator, so as to take into account all the physical phenomena (capillary pressure, gravity) that influence the experimental data obtained. Such an interpretation is for example described in the above-referenced French patent 2,708,742 and corresponding U.S. Pat. No. 5,679,885.

These patents also describe a device allowing carrying out this type of multi-flow displacement experiments.

As regards determination of the electric parameters, the most common approach also carries out displacement experiments at a fixed flow rate or pressure. The resistivity of a solid sample can be measured by means of electrodes that are in contact with the surface thereof, at selected points, and between which an electric current is passed. The measurement of the potential difference appearing between the locations of the electrodes directly gives the resistivity measurement. Contact of the electrodes with the surface has to be the best possible for the measurements to be representative. A known method places the sample to be tested in an elastic flexible sheath. The electrodes are arranged between the sample and the sheath, and connected therethrough, by electric conductors, to an electrical conductivity measuring system. The sheath is placed in a containment vessel. A fluid under pressure is allowed into the vessel, which has the effect of pressing the sheath and consequently the electrodes against the sample. Such a method using a fluid under pressure for pressing a sheath against a sample is used for example in the petrophysics tools described in French Patent 2,708,742 and corresponding U.S. Pat. No. 5,679,885 and French Patent 2,724,460 and corresponding U.S. Pat. No. 5,610,524, or in U.S. Pat. No. 5,105,154.

A device allowing such displacement experiments to be carried out at a fixed flow rate is for example described in French Patent 2,708,742 and corresponding U.S. Pat. No. 5,679,885, and a device allowing such experiments at a centrifugation-imposed pressure is described in French Patent 2,758,881 and corresponding British Patent 2,322,942. Furthermore, French Patent 2,778,449 describes a device allowing carrying out such resistivity measurements under reservoir conditions while measuring and controlling the capillary pressure levels in the rock during drainage phases. This allows plotting the evolution of the resistivity index as a function of the brine saturation of the sample. A ceramic arranged at the sample outlet allows reaching very low saturation levels, which is extremely useful to cover the saturation range of a large number of reservoirs. The resistivity data are then directly used by logging engineers to estimate the initial oil saturations and therefore the amounts of oil in place. Besides, this device is also used to obtain the same type of results during imbibition phases (spontaneous and forced). The brine is then injected into the sample at an imposed flow rate through the ceramic. Several phases with increasing injection rates are generally carried out so as to decrease the oil saturation in the sample down to its residual value. The amount of hydrocarbons is then determined from these electric resistivity measurements. The principle is based on the fact that the resistivity of a brine or oil saturated sample depends on the water saturation because oil is not a conducting fluid.

Evaluation of the flow parameters (krs) and of the electric parameters thus requires different equipment, and therefore different samples for each device. Now, evaluation of the content and of the productivity of an underground reservoir requires coherence between the measurements performed on these various samples.

The method and the device according to the invention allow evaluation of the multiphase flow parameters, the capillary effects being entirely and precisely taken into account, and of the electrical parameters of a porous medium, with the same type of equipment, the same experiment and from the same rock sample taken from this medium.

SUMMARY OF THE INVENTION

The invention relates to a method for simultaneously evaluating the measured electrical resistivity and the flow parameters of a porous medium, from at least one multi-flow type displacement experiment. This type of experiment injects a first injected fluid into a medium sample initially saturated with a second displaced fluid wherein the injection rate of the injected fluid is increased at least once after a step of stabilization of the displaced fluid production volume.

The method and the device can find applications in many fields, notably for the study of oil-bearing reservoirs. The invention then relates to the measurement of the relative permeability curves that control the dynamic behavior of oil reservoirs and the electrical measurements used for calibration of logging tools intended to evaluate the amount of hydrocarbons in the reservoir. Evaluation of the content and of the productivity of an underground reservoir is obtained for example by means of numerical simulations from measured or determined values of certain parameters of the rocks such as the capillary pressure and the relative permeability thereof for the fluids present therein. These parameters are generally measured in the laboratory from rock samples taken in situ by core drilling.

The method according to the invention comprises the following stages:

continuously measuring as a function of time the differential pressure between two ends of the sample ($\Delta P^i(t)$) and the electric resistivity of the sample (R(t));

measuring for each stabilization step the displaced fluid production volume (V($t_1$), V($t_2$));

estimating a relation between the electrical resistivity of the sample and the displaced fluid production volume, from the resistivity measurements (R(t)) and the displaced fluid production volume values (V($t_1$), V($t_2$));

establishing a continuous curve of the displaced fluid production volume as a function of time (V(t)), from said relation;

estimating flow parameters from the continuous differential pressure measurement ($\Delta P^i(t)$) and from said continuous curve (V(t)) by means of a numerical flow simulator.

The relation between the electrical resistivity and the displaced fluid production volume can furthermore be estimated from a resistivity curve as a function of the sample saturation at the end of the step.

According to the invention, the electrical resistivity can be measured by arranging radially electrical resistivity measuring electrodes around the sample and using a relatively short sample, of a length of the order of 3 cm.

The invention also relates to a device for carrying out, on a porous solid sample (S), multi-flow displacement experiments. This device comprises a containment vessel (1) containing the sample (S) saturated with a first fluid, referred to as displaced fluid, closed at one end by a first cylindrical end part (16) connected to means (5a and 5b) for injecting under pressure a second fluid, and referred to as injected fluid, and closed at the other end by a second cylindrical end part (15) comprising a fluid circulation system (4a, 4b and 4c). The device according to the invention comprises:

a semi-permeable porous plate (C) arranged between the sample and the first end part;

means (6) for continuously measuring the electrical resistivity of said sample;

means (3) for measuring the displaced fluid production volume for each stabilization step;

means (22 and 23) for continuously measuring the differential pressure of one of the fluids on either side of the sample, between the sample and the semi-permeable porous plate.

According to the invention, the first cylindrical end part can comprise a first cylinder (18) arranged in a second concentric cylinder (17).

The means allowing continuous measurement of the differential pressure can comprise at least one pressure measuring line (22) connected to a differential pressure sensor (23), and this line can comprise a series of longitudinal slots (27) machined in the inner surface of the second cylinder (17) or in the outer surface of said first cylinder (18).

Finally, according to the invention, the pressure measuring line can be designed to prevent air trapping when installing the first end part.

BRIEF DESCRIPTION OF THE DRAWINGS

Other features and advantages of the method according to the invention will be clear from reading the description hereafter of embodiments given by way of non limitative examples, with reference to the accompanying figures wherein.

DETAILED DESCRIPTION OF THE INVENTION

1. The Device

The device according to the invention allows carrying out, on a single sample taken from a porous medium, multi-flow displacement experiments during which it is possible to perform petrophysical measurements (resistivity, saturation, differential pressure, . . . ) allowing simultaneous evaluation of the multiphase flow parameters (relative permeabilities) and the resistivity curve.

Figure 1:
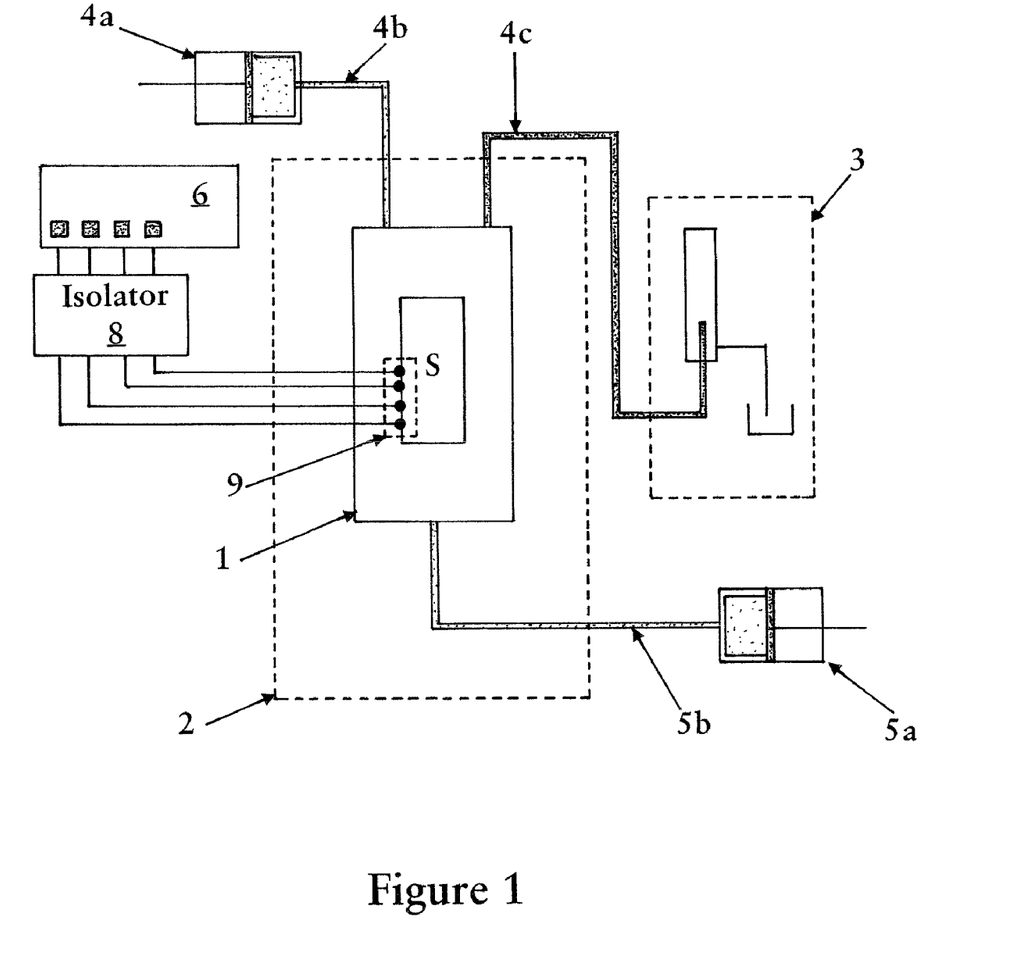
FIG. 1 diagrammatically shows a device allowing multi-flow displacement experiments to be carried out.

This device is diagrammatically shown in FIG. 1. It comprises an elongate containment vessel 1 that can be cylindrical and contains the sample to be tested S. This vessel is arranged within a thermostatically controlled enclosure 2 whose temperature can generally rise up to 150° C. The upper face of vessel 1 is equipped with a system allowing a fluid circulation leading to sweeping of the upper face of the sample. In fact, to be precise, the outlet face of the sample is swept at a high flow rate by brine in a closed circuit so as to rapidly circulate the integrity of the oil produced from the sample to a system 3 allowing determination of the volume of fluid expelled and comprising an oil level detection and separation system such as graduated burets. This circulation system is made up of a high flow rate HFR pump 4a that injects brine towards the upper surface of the sample through a channel 4b and a channel 4c from which the brine and the oil are discharged from the face of the sample to an oil level separation and detection system 3. At the opposite face, the device comprises a low flow rate LFR pump 5a that injects brine towards the lower surface of the sample through a channel 5b. The device also comprises a resistivity measuring device of a well-known type ("LCR meter") 6, an isolator 8 and electrodes 9 in direct contact with sample S.

Figure 2:
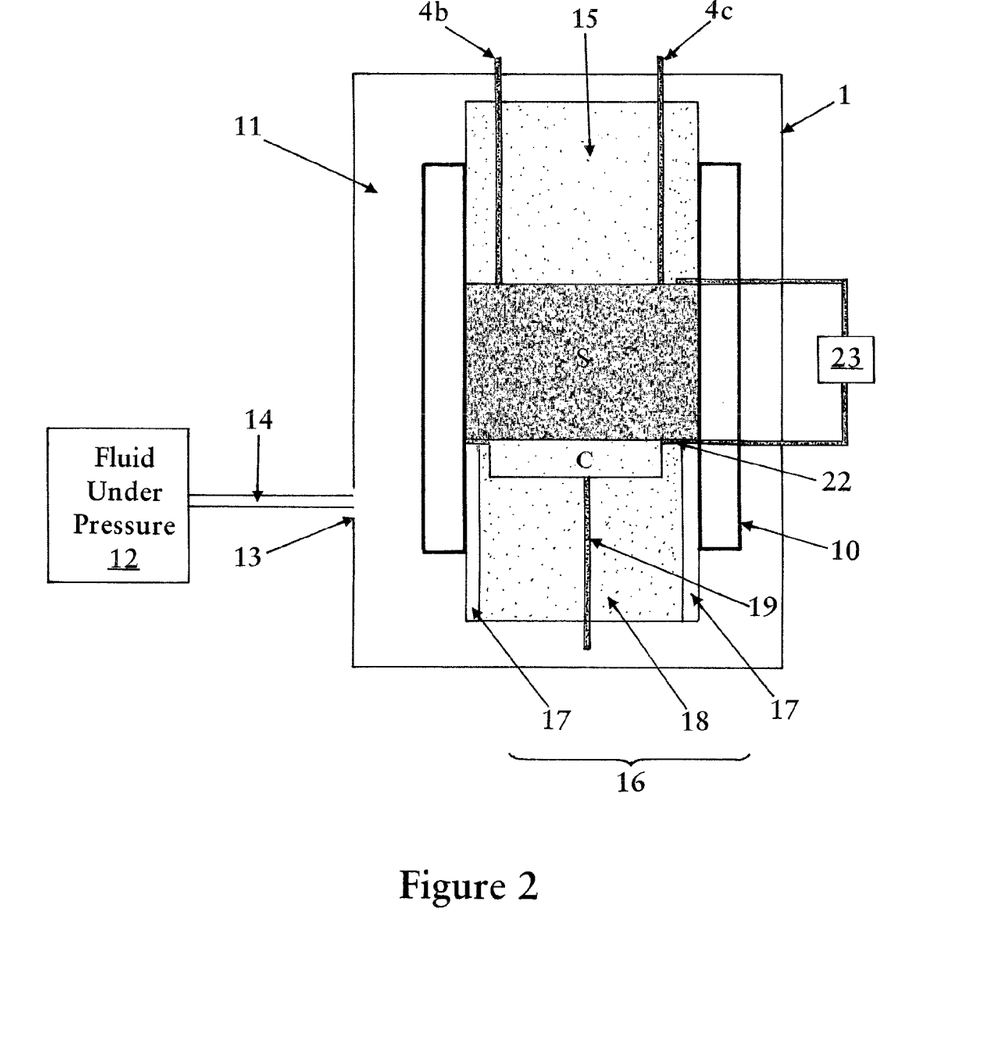
FIG. 2 illustrates in detail containment vessel (1) of the device according to the invention.

FIG. 2 illustrates more in detail the device at the level of the containment vessel. The sample to be tested S is placed within a deformable sheath 10 and the assembly is arranged in enclosure 1. Annular space 11 around sheath 10 communicates with a source 12 of fluid under pressure for delivering fluid through an opening 13 provided in the outer wall of enclosure 1 and through a line 14 connected to this opening. It can be a compressed gas bottle, a jack or a hydraulic pump. Application of this fluid allows the sample to be tested to be subjected to a predetermined pressure.

A semi-permeable porous plate C (impermeable to the displaced fluid contained in the sample but permeable to the injected fluid) such as a ceramic for example, is arranged at the base of sample S, that is at the level of the injection face, to obtain extremely low saturation levels as described in French patent application 03/15,199 filed by the assignee.

The device according to the invention comprises two cylindrical end parts 15 and 16 allowing the containment vessel to be closed with an upper end part 15 (sweep end part) located at the top of the sample, on the fluid circulation side, and a lower end part 16 (injection end part) located at the base of the sample, on the fluid injection side.

Sweep end part 15 is a cylinder made of a highly stainless steel such as hastelloy. Through this cylinder, the two channels 4b and 4c are positioned parallel to the axis of the enclosure.

The injection end part comprises two concentric cylinders 17 and 18. The first cylinder, 17, which is hollow, is permanently in contact with the sheath. It allows removal of the second cylinder 18, which is solid, without modifying the pressure conditions exerted by the sheath on the sample. This first cylinder therefore has a diameter that is substantially equivalent to that of the sample. The size of the wall thereof has to be sufficiently large so as not to deform under the effect of the pressure exerted by the sheath, but sufficiently small for the second cylinder, whose base has a larger surface area than the ceramic, to be fitted therein. This second cylinder 18 is described in detail in FIG. 3. It is also made of a highly stainless steel such as hastelloy. It comprises a channel 19, parallel to the longitudinal axis thereof, running right through the cylinder, and into which a fluid can be injected. On the side in contact with the sample, the cylinder is provided with a cavity 20 allowing containment of ceramic plate C while providing contact between the plate and the sample.

Figure 3:
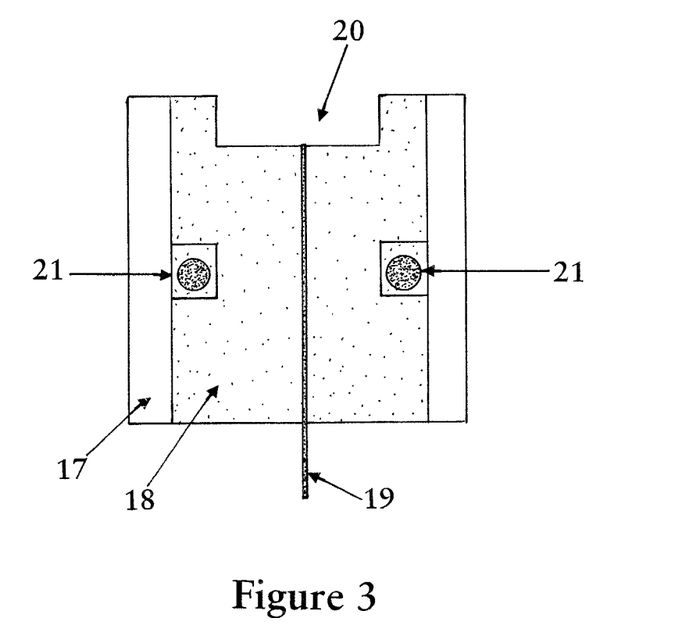
FIG. 3 illustrates in detail injection end part (16) of the device according to the invention.

Sealing between the two cylinders of injection end part 16 is provided by O rings 21 arranged between the two cylinders.

The presence of the semi-permeable ceramic allows obtaining extremely low saturation levels. On the other hand, it is a major drawback regarding determination of the relative permeabilities. In fact, because of its low permeability, the differential pressure generated on the "ceramic+sample" assembly is so high that measurement of the global differential pressure does not allow detection of the response of the sample wherein the differential pressure produced on the sample itself is very low in comparison. This makes the correction of a global differential pressure measurement (ceramic and sample) difficult and not very precise in practice.

The device according to the invention is therefore provided, at the level of the injection end part, with a pressure measuring line 22 (FIG. 2) between the sample and the ceramic, allowing, by means of a differential pressure sensor 23, measuring the differential pressure produced on the sample itself and not on the "ceramic+sample" assembly.

According to a first embodiment, the second cylinder comprises this pressure measuring line 22 between the sample and the ceramic allowing measurement of the differential pressure produced on the sample itself.

According to a second embodiment (FIG. 4), this second cylinder is also provided with a circular slot 24 perpendicular to the cylinder axis. This slot is provided at a height between ceramic C and joints 21 and has at least a second channel 25 parallel to the longitudinal axis thereof, running therethrough from its base to a height between circular slot 24 and joints 21. This second channel 25 communicates with circular slot 24 via channel 26 and vertical slot 27. Finally, in this cylinder, at the level where this second channel stops, at least a third channel 26, perpendicular to the cylinder axis, allows connection of second channel 25 to the cylinder periphery, between the sample and the joint. At least one line comprising vertical slots 27 (parallel to the cylinder axis) going from the sample (on the periphery of the porous plate) and stopping at third channel 26 is arranged between the two cylinders. At least one of these slots communicates with the third channel. According to the embodiment of FIG. 4, there are four such slots and they are arranged evenly on the periphery of the cylinders. Depending on the embodiments, these vertical slots can be provided either on the surface (necessarily the outer surface because the cylinder is solid) of central cylinder 18 or on the inner surface of peripheral cylinder 17.

In this second embodiment (FIG. 4), pressure measuring line 25 is the line coupled to the vertical slots 27 via the third channel. In fact, this line allows the pressure to be measured between the ceramic and the sample, and it can be measured at the outlet of channel 25.

Figure 4:
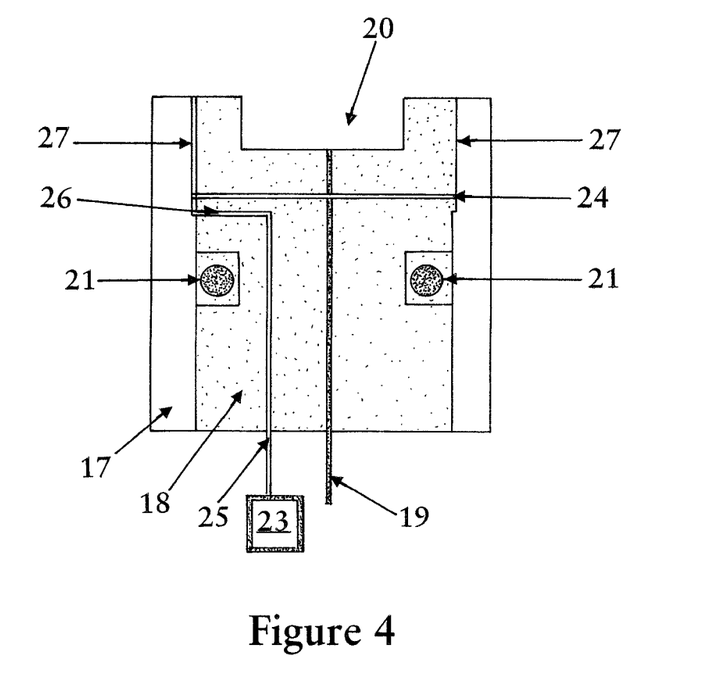
FIG. 4 illustrates an embodiment of the device according to the invention wherein second cylinder (18) is provided with slots (24 and 27) and channels (19, 25 and 26) allowing pressure measurements between the ceramic and the sample.

The injection end part 16 is provided with slots 27 allowing cylinder 18 to be moveable which do not trap air.

This device also allows measurement of the differential pressure on the sample during the experiment without taking account of the ceramic, using pressure measuring device 23 arranged at the outlet of second channel 25 parallel to the cylinder axis.

The device, under reservoir conditions, carries out multi-flow displacement experiments while performing:

continuous sample electrical resistivity measurements denoted by R(t), by means of device 6;

time-based measurements of the displaced fluid production volume for each injection step, denoted by $V(t_1), V(t_2), \ldots$), by means of system 3; and continuous differential pressure measurements, for one of the fluids, on either side of the sample, denoted by $\Delta P^i(t)$, by means of differential pressure sensor 23 and pressure measuring line 25 arranged between the ceramic and the sample.

This device works as follows:

The case of an initially oil-saturated sample, for example, is considered that is placed in an enclosure 1 and pressurized by injection of a fluid into annular space 11 around sheath 10. By means of pump 5a, through channel 5b, water is injected under pressure, with a fixed flow rate, at a first end of the sample. At the opposite end, a water circulation (4a, 4b and 4c) is established at a constant high pressure (atmospheric pressure for example, or a fixed pressure imposed by a fluid tank at a reference pressure) and with a low flow rate. This water is pumped by system 3. The water is injected by pump 4a into channel 4b, and it leaves through channel 4c, carrying along the fluids (water and oil) as they are expelled from sample S. Continuity is thus provided throughout between the circulating fluid and the oil expelled from the sample.

2. Measurements Interpretation Method

The method according to the invention allows this device to be used in order to evaluate relative permeability curves despite the presence of the ceramic and the limited length of the sample used (typically of the order of 3 cm) while the capillary effects are completely and precisely taken into account. The method allows simultaneous determination of the amount of displaced fluid in place in the medium.

Within the context of the description, a particular application is chosen that injects brine into a predominantly oil-saturated sample with a reduced brine saturation. This method is applied within the scope of petroleum exploration in order to determine the krs curves or to vary the water saturation in a sample. The fluids could however be reversed or two immiscible fluids could be used without departing from the scope of the invention.

Stage 1: Multi-Flow Type Displacement Experiment and Petrophysical Measurements

A known multi-flow type displacement experiment is described for example in:

Egermann P. and Lenormand R., "*A New Methodology to Evaluate the Impact of the Local heterogeneity on Petrophysical Parameters (kr, Pc): Application on Carbonate Rocks*", SCA n° 2004-18, Society of Core Analysts, Abu Dhabi, 2004 is first carried out.

The method essentially places a solid sample (S) saturated with a first fluid (oil for example) in a closed containment vessel (1), injecting at a flow rate fixed by pressure means (5a, 5b) another fluid under pressure (a brine for example) at a first end of the enclosure, and sweeping the opposite end with a high-pressure fluid circulated by pumping means (4a, 4b, 4c), which causes the drained fluid to be expelled.

Then, a new injection is performed with a different flow rate. The number of injections depends on the desired quality and time for obtaining the measurements.

During this experiment, the following measurements are performed:

continuous sample electrical resistivity measurements, denoted by R(t);

punctual displaced fluid production volume measurements for each injection step, denoted by $V(t_1), V(t_2), \ldots$); and continuous differential pressure measurements, for one of the fluids, on either side of the sample, denoted by $\Delta P^i(t)$.

Stage 2: Determination of a Continuous Displaced Fluid Production Volume Curve as a Function of Time A continuous curve of the displaced fluid production volume as a function of time V(t) is established. The device according to the invention allows performing time-based measurements of the displaced fluid production volume $V(t_1), V(t_2), \ldots$. It is then possible to directly estimate from these punctual measurements a continuous curve V(t). However, no a priori information is available on the shape of curve V(t). Furthermore, since only a limited number of displaced fluid production volume measuring points $V(t_1), V(t_2), \ldots$ is available, estimation of a complex curve cannot be expected. The method according to the invention therefore takes advantage of the continuous measurements of the electrical resistivity of the sample, which gives the "course" of curve V(t). From known pairs for these two types of value, it is possible to determine a law relating the resistivity to the displaced fluid production volume. This determination can be performed, for example, by means of a regression because this relation is linear or quasilinear, which allows making less errors on this estimation than on the direct estimation of curve V(t). Then, this law is applied to convert the continuous resistivity measurements to a continuous curve of the displaced fluid production volume as a function of time V(t).

The various parameters are conventionally expressed as a function of the saturation of one of the fluids in the petrophysical sphere. Thus, if either the capillary pressures, the relative permeabilities or the resistivity measurements are to be represented, these quantities are represented as a function of the saturation because it is a quantity that does not depend on the pore volume. This allows a comparison of the results obtained on various samples whose macroscopic properties are never exactly the same.

This is the reason why, according to an embodiment, a resistivity curve as a function of saturation is established prior to the continuous curve of displaced fluid production volume as a function of time V(t).

Mean injected fluid ($\overline{S}_w$) and displaced fluid ($\overline{S}_o$) saturation values are therefore deduced from the displaced fluid production volume values $V(t_1), V(t_2), \ldots$ measured at the end of each injection period and from the injected fluid volume ($V_w(t_1), V_w(t_2), \ldots$):

$$\overline{S}_w = 1 - \overline{S}_o = S_{wi} + \frac{V_w}{VP}$$

with: $S_{wi}$ the initial injected fluid saturation.

VP the pore volume of the sample (measured beforehand, for example by means of an NMR technique).

From known saturation and resistivity pairs, it is possible to determine a law relating the resistivity to the saturation. This determination can be performed, for example, by means of a linear regression or of a non-linear regression. Then, this law is applied to convert the continuous resistivity measurements to a continuous saturation curve as a function of time.

Then, the continuous curve of displaced fluid production volume as a function of time is logically deduced from this curve.

It can be noted that, in order to establish such curves, the time-based electrical resistivity value used has to be as insensitive as possible to the saturation profiles of the sample. These relations are therefore obtained preferably with a radial geometry of measuring electrodes and a short sample.

Stage 3: Estimation of the Multiphase Flow Parameters

Multiphase flow parameters are estimated from continuous differential pressure measurements and from the continuous curve of displaced fluid production volume as a function of time. Many techniques known in the art allow this stage to be carried out. The method described by Egermann and Lenormand can for example be used:

Egermann P. and Lenormand R., "*A New Methodology to Evaluate the Impact of the Local Heterogeneity on Petrophysical Parameters (kr, Pc): Application on Carbonate Rocks*", SCA n° 2004-18, *Society of Core Analysts, Abu Dhabi*, 2004.

However, concerning the interpretation of the measurements obtained from the device according to the invention, the delicate point is the short length of the sample. The samples conventionally used for determining multiphase flow parameters are generally longer (6-10 cm). Because of this short length, the capillary effects have to be completely taken into account to obtain coherent and representative results in terms of relative permeabilities, allowing accounting for the non-uniformity of the saturation profile. The most suitable injection procedure is based on a multi-flow injection while waiting for stabilization of the displaced fluid production volumes, which allows collecting information on the capillary pressure and the relative permeabilities of the injected phase analytically before passage to the numerical simulator.

Analytical Interpretation of the Results:

The stage of experimental data analytical interpretation is described in the French patent application 04/09,273. By knowing the state of stabilization (of the displaced fluid production volume) corresponding to an equilibrium between the viscous forces and the capillary forces, it becomes possible to evaluate, for a given saturation value, the mean value of the capillary pressure on the scale of the sample analyzed, denoted by Pc, the mean value of the injected fluid relative permeability, denoted by $kr_{inj}$, and the mean value of the displaced fluid relative permeability, denoted by $kr_{dep}$. It is therefore possible to use for example the expressions developed within the scope of the semi-dynamic method described in French Patent 2,708,742 and corresponding U.S. Pat. No. 5,679,885. In this method, the saturation at the inlet of the sample ($S^i$) is determined by means of the following formula:

$$S^i(\Delta P^i) = \overline{S} + q \frac{d\overline{S}}{dq} \quad (1)$$

where:
$S^i$ is the saturation at the inlet;
q is the flow rate of the fluid injected into the sample;
$\Delta P^i$ is the differential pressure measured at the sample inlet; and
$\overline{S}$ is the mean saturation of one of the fluids. $\overline{S}$ can be calculated from the displaced fluid production volume measured at the sample outlet ($V(t_1), V(t_2), \ldots$).

At the end of each injection period, when stabilization is reached, it is important to note that the pressure of the displaced fluid is uniform and equal to outlet pressure ($P_{dpp}^{\,o}$).

Thus, the local pressure of the injected fluid directly corresponds to the capillary pressure plus the outlet pressure. In cases where stabilization of the displaced fluid production volume is not quite reached (non-uniform pressure in the displaced fluid), it can be noted that the pressure profiles in the two fluids are smooth and that it is also possible to use directly the simulated capillary pressure profiles to deduce the local properties.

Thus, at the sample outlet, the injected fluid pressure is considered equal to the displaced fluid pressure. Insofar as the capillary pressure is defined as the difference between these two pressures, the outlet capillary pressure ($P_c^{\,o}$) is zero: $P_c^{\,o}=0$.

At the sample inlet, if the displaced fluid pressure is zero ($P_{dep}^{\,o}=0$), the inlet differential pressure, which corresponds to the inlet pressure of the injected fluid, is equal to the inlet capillary pressure ($P_c^{\,i}$): $P_c^{\,i}=\Delta P^i$ ($P_c^{\,i}=\Delta P^i+P_{dep}^{\,o}$ if $P_{dep}^{\,o} \neq 0$).

Thus, at each step, an inlet saturation $S^i$ is calculated, and the inlet differential pressure, which corresponds to the inlet capillary pressure, is measured. A set of pairs, $(S^i; P_c)$, one for each step, is thus obtained.

$kr_{inj}$ is determined by means of the following formula, for a given inlet saturation and therefore a given $\Delta P^i$ (for each step):

$$kr_{inj} = \frac{\mu L}{KA} \frac{dq}{d\Delta P^i} \quad (2)$$

where:
μ is the viscosity of the injected fluid;
L is the length of the sample;
K is the permeability; and
A is the injection surface area.

The quantity $kr_{dep}$ can be determined using a JBN type interpretation known in the art, described for example in the following document:

Johnson E. F., Bossier D. P. and Naumann V. O.: "*Calculation of Relative Permeability from Displacement Experiments*", Trans. AIME, 216, 370-372, 1959.

This method requires measurement of outlet saturation $S^o$.

A saturation $S^i, P_c^{\,i}(S^i)$, $kr_{inj}(S^i)$ and ($kr_{dep}(S^o)$ is thus obtained for each injection step. All of the displaced fluid and injected fluid relative permeabilities will be denoted by krs.

Numerical Interpretation of the Results:

After evaluating, at each step, a saturation value ($S^i$), a mean capillary pressure value ($P_c^{\,i}(S^i)$), an injected fluid relative permeability value ($kr_{inj}(S^i)$) and a displaced fluid relative permeability value ($kr_{dep}(S^o)$), a stage of numerical interpretation of the experimental measurements is carried out. The procedure is as follows:

determining, for example by means of centrifugation experiments known in the art, a curve of mean capillary pressure values as a function of saturation, on a sample close to the sample studied and having similar properties. This curve is denoted by $P_c^{\,V}(S)$;

refining curve $P_c^{\,V}(S)$. A first method takes into account the permeability, porosity and interfacial tension variations by means of the Leverett function. This function is described in the following documents:

Leverett M. C.: "*Capillary Behavior in Porous Solids*", Trans. AIME, 142, 152-168, 1941.

Leverett M. C., Lewis W. B. and True M. E.: "*Dimensional Model Studies of Oil-Field Behavior*", Trans. AIME, 146, 175-193, 1942.

A second method uses the results of the analytical interpretation from the multi-flow displacement experiment. In fact, this stage allows calculation of capillary pressure values ($P_C^i(S^i)$) for a certain saturation number (inlet capillary pressure and inlet saturation for each injection step). It is possible to normalize capillary pressure curve $P_C^V(S)$ from these points, that is curve $P_C^V(S)$ is deformed so that it passes through these points precisely calculated on the sample studied. This normalized curve is denoted by $P_C(S)$.

Then, by means of $P_C(S)$ and of the initial set of krs from the analytical interpretation of the experimental data, a flow simulator is used to calibrate experimental data ($\Delta P^i(t)$ and $V(t)$) by deforming the krs curves until the minimum of an objective function is obtained.

At the end of this numerical interpretation stage, a set of krs is obtained corresponding to the calibration of the differential pressure ($\Delta P^i(t)$), the production volume curves ($V(t)$), and that takes into account the end capillary effects.

Example of Application to a Real Case

General Data

The example considered was conducted on a carbonate rock of low permeability under reservoir conditions (101° C.). The characteristics of the sample and of the fluids (oil and brine) are given in Table 1.

TABLE 1 characteristics of the sample and of the fluids

| | |
|---|---|
| Length (cm) | 3.12 |
| Diameter (cm) | 3.98 |
| Porosity (%) | 20.6 |
| PV (cm³) | 8 |
| Initial brine saturation $S_{wi}$ (%) | 46 |
| Absolute permeability (md) | 0.13 |
| Oil viscosity at 101° C. (cP) | 1.8 |
| Brine viscosity at 101° C. (cP) | 0.45 |

Stage 1: Multi-Flow Displacement Experiment and Electric Measurements

Three periods with distinct brine injection flow rates were considered during the experiment: 0.1, 0.2 and 1 cm³/h. These relatively low flow rates were selected so as to progressively raise the pressure in order to gradually explore the capillary properties of the sample.

Stage 2: Determination of a Continuous Curve of Displaced Fluid Production Volume as a Function of Time In this example, the continuous curve of displaced fluid production volume as a function of time was obtained from a resistance curve $R_e$ (from the resistivity measurements) as a function of saturation.

Figure 5:
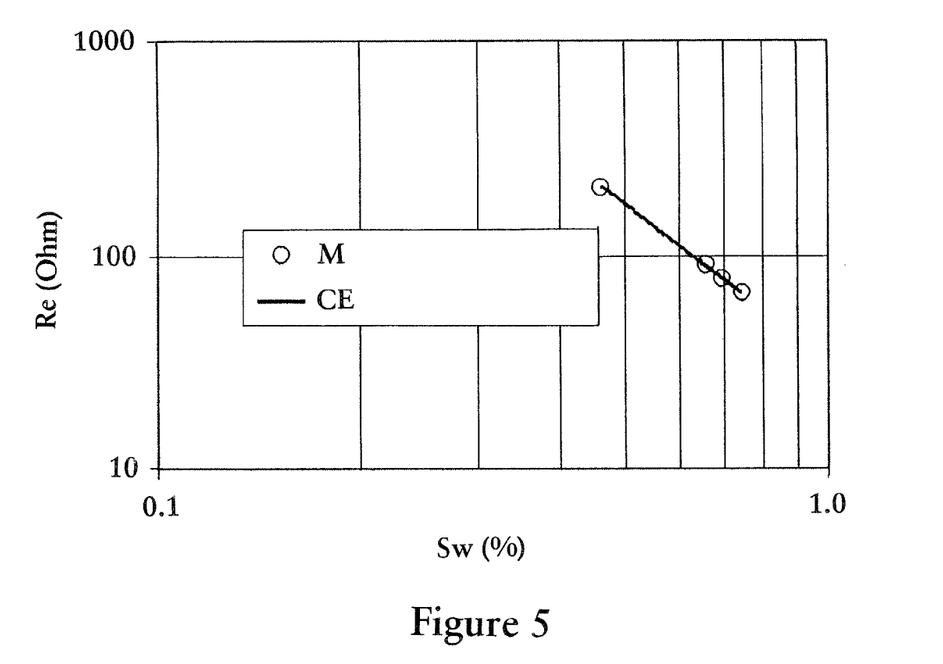
FIG. 5 shows the saturation points (M) obtained at the end of the injection stage as a function of the corresponding resistance measurements (Re), as well as the resistance curve (CE) as a function of the brine saturation (Sw)

FIG. 5 shows a comparison between the saturation points (deduced from the displaced fluid production volume) obtained at the end of the injection period for a given flow rate and the corresponding resistance measurements (M). A very good correlation can be observed between these two measurements, which allows proposing a power type law for resistance curve $R_e$ as a function of saturation:

$$R_e = 33.74 S_w^{-2.33}$$

FIG. 5 shows the resistance ($R_e$) as a function of brine saturation (Sw). The circles represent measuring points (M) and the full line represents the power type law selected for resistance curve $R_e$ as a function of saturation (CE).

Figure 6:
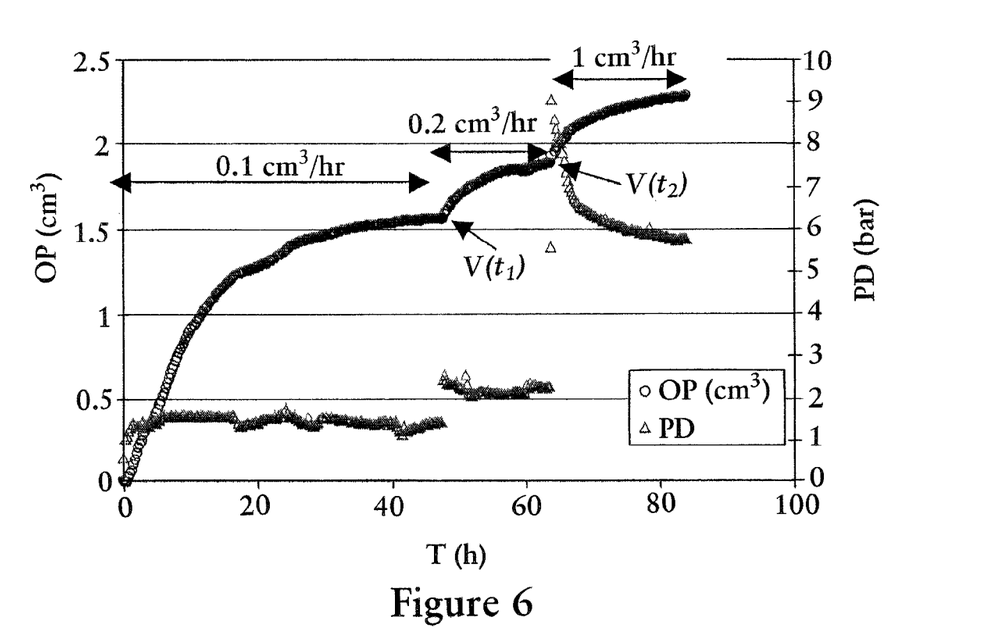
FIG. 6 illustrates, for each one of the three flows, the production volume (OP) and differential pressure (PD) curves as a function of time.

Continuous resistance measurement then allows calculation of the evolution of the mean saturation as a function of time, which is thereafter converted in terms of production volume in order to obtain a more standard representation in terms of relative permeability. FIG. 6 illustrates, for each one of the three flow rates, the production volume curves (OP) obtained as a function of time (T) and the differential pressure curves (PD) obtained by continuous measurement. The punctual measurements of the displaced fluid production volume $V(t_1), V(t_2)$ are also shown for the first two stabilization steps.

The curves which are obtained are conventional curves of a multi-flow injection experiment with additional oil production at each flow rate increment (bump). After an increase upon flow rate change, the differential pressure then decreases progressively as oil is produced. The slight differential pressure fluctuations are due to temperature variation effects in the laboratory, which have been identified and corrected.

Stage 3: Estimation of the Multiphase Flow Parameters

1. Analytical Interpretation

Figure 7:
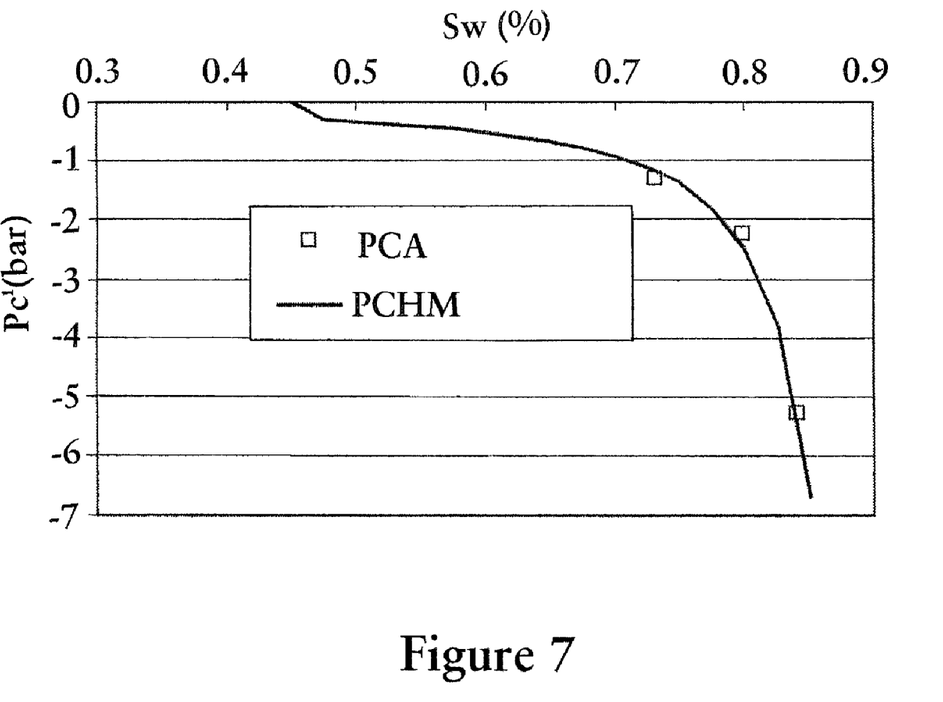
FIG. 7 shows three capillary pressure points obtained analytically (PCA) as a function of the saturation (Sw), as well as a capillary pressure analytical law (PCHM) of power law type.

For each step, a mean brine saturation $S_w$ is calculated and the inlet differential pressure that corresponds to the inlet capillary pressure ($P_c^i$) is measured. A set of pairs, ($S_w; P_c^i$), one for each step, is thus obtained. Within the context of this experiment, three analytical points corresponding to the three flow rates of the forced part of the imbibition are thus obtained. FIG. 7 shows these three capillary pressure points obtained analytically (PCA) as a function of saturation ($S_w$). The rounded shape suggested by the analytical points shows that the sample has at least a partial oil wettability. The points were used as a basis for calibration of an analytical capillary pressure law (PCHM), of power law type, so as to introduce a continuous curve in a flow simulator to carry out the simulation. This curve is also illustrated in FIG. 7.

Figure 8A:
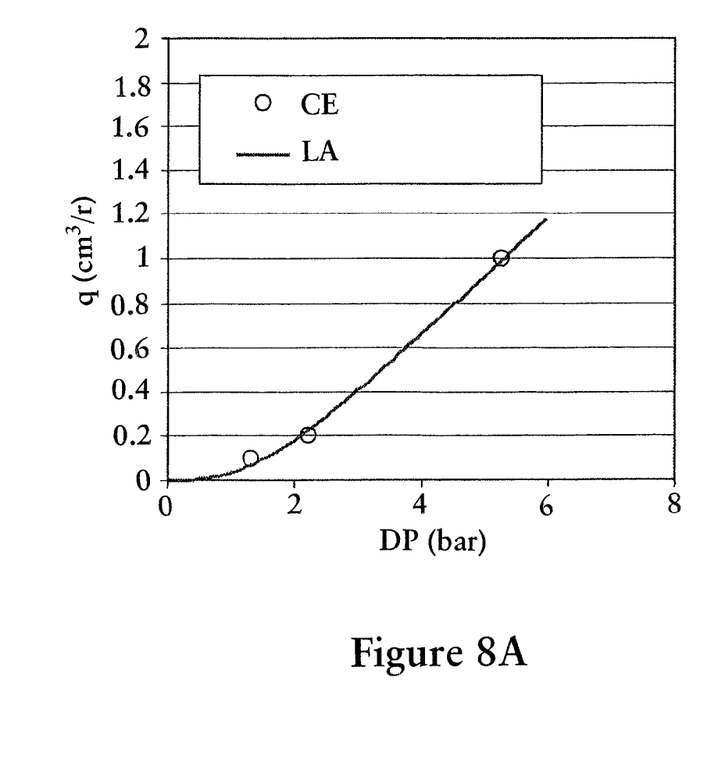
FIG. 8A shows three experimental pairs (CE) of injection rate (q) and differential pressure (DP) values, as well as the result of an exponential type analytical expression (LA)
Figure 8B:
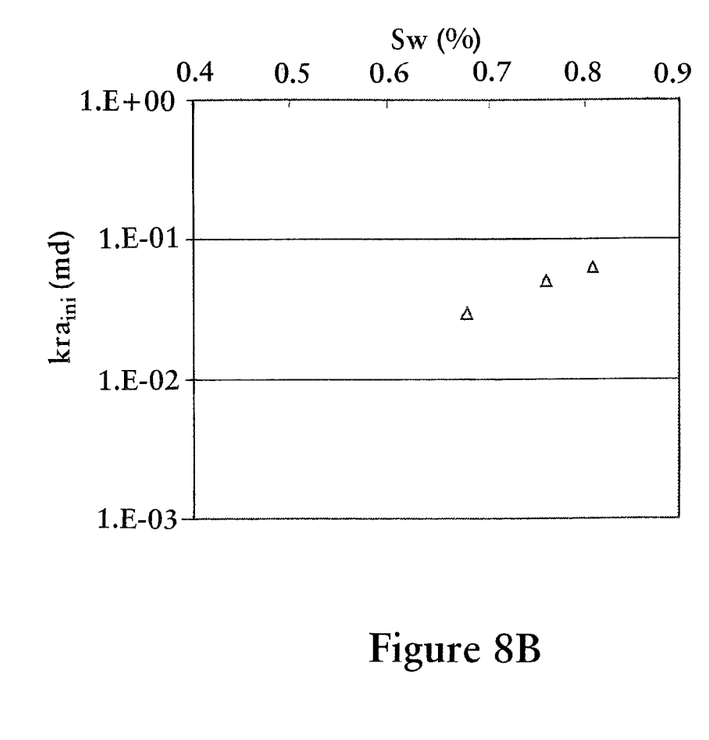
FIG. 8B illustrates the results obtained in terms of analytical $kr_{inj}$ ($kr_{inj}$) as a function of saturation ($S_w$)

Analytical calculation of $kr_{inj}$ ($kra_{inj}$) requires the values of the derivative of injection flow rate q with respect to the differential pressure. FIG. 8A shows the three experimental pairs (CE) of injection flow rate (q) and differential pressure (DP) values, as well as the result of an analytical expression of exponential type (LA) without manual derivative calculations. The results obtained which are in terms of analytical $kr_{inj}$ ($kra_{inj}$), show in FIG. 8B that the limit point of $kra_{inj}$ at Sorw (residual oil saturation) remains low, below 0.1.

2. Numerical Interpretation

Figure 9:
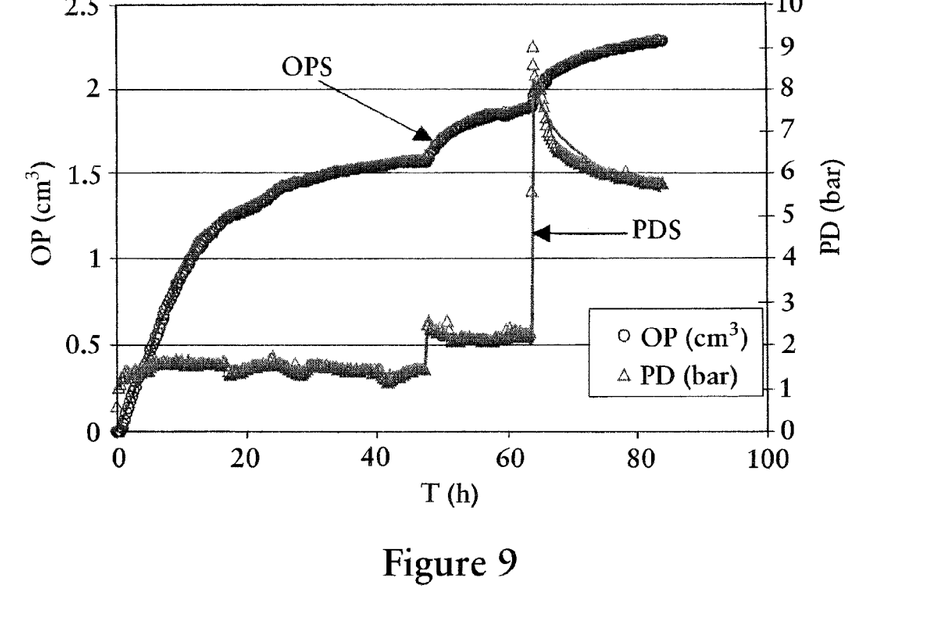
FIG. 9 illustrates the calibration of the experimental data by giving, for each one of the three flow rates, the simulated production volume curves (OPS) as a function of time and the simulated differential pressure curves (PDS)

All of the above parts were used as a basis for completing a set of data for the flow simulator utilizing an inversion of the relative permeabilities (krs). Inversion allows obtaining a set of simulated relative permeabilities (krs) in good accordance with the experimental data. FIG. 9 illustrates this experimental data calibration. This figure takes up FIG. 6 representing, for each one of the three flow rates, the simulated production volume curves (OPS) as a function of time and the simulated differential pressure curves (PDS).

Figure 10:
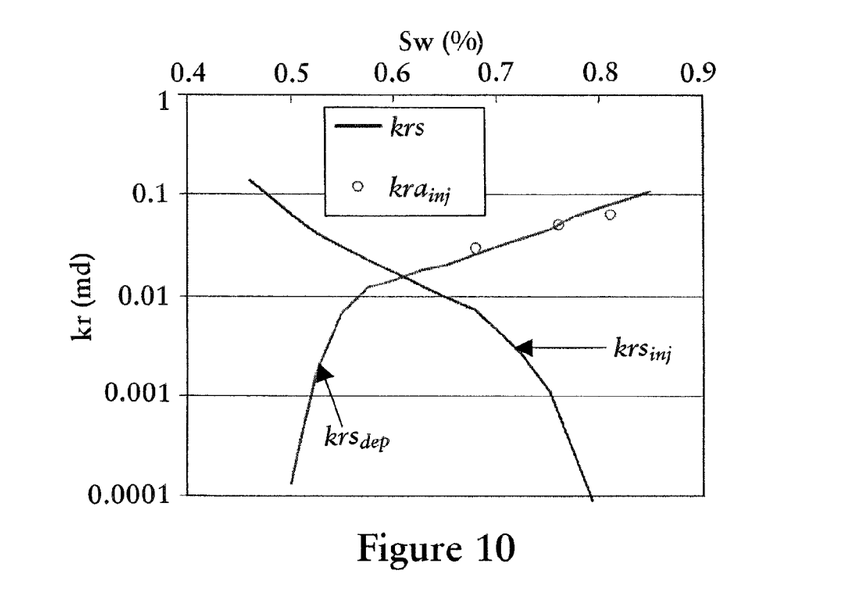
FIG. 10 illustrates the relative permeability curves (krs) obtained after simulation.

The relative permeability curves (krs) obtained after simulation have a quite conventional course, as can be seen in FIG. 10. The initial point of the $krs_{dep}$ curve is rather low (0.14) because of the presence of a high brine saturation at the beginning of the experiment (0.46). A good coherence with the $krs_{inj}$ points calculated analytically ($kra_{inj}$) is also observed.

Validation

Figure 11:
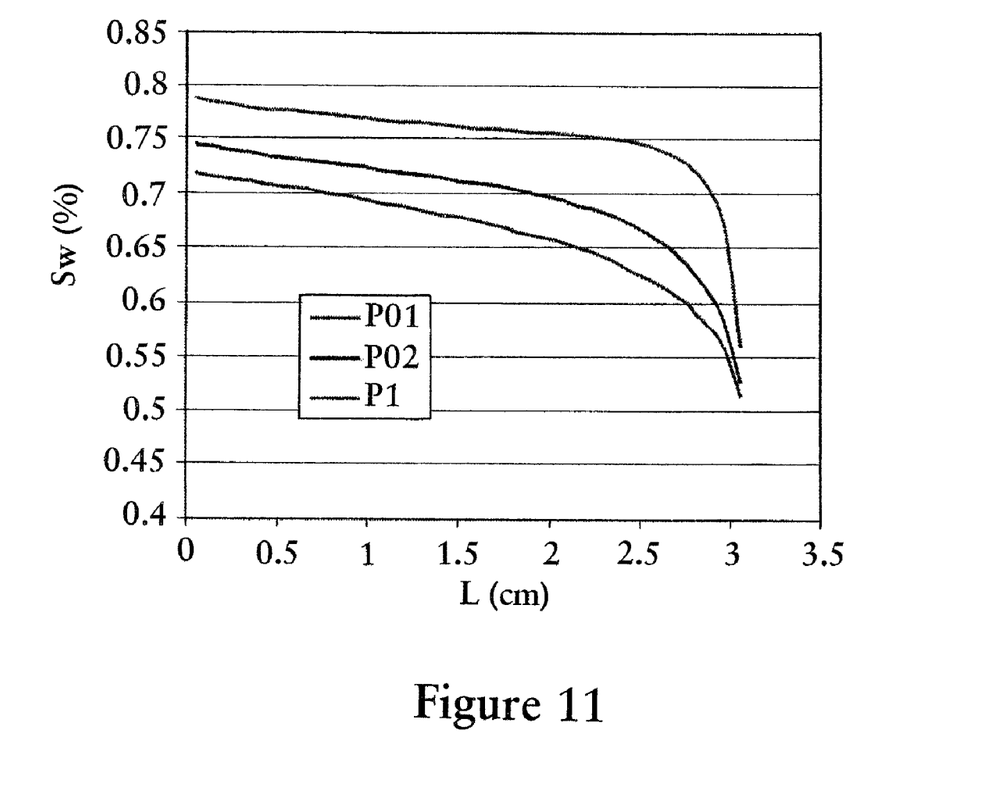
FIG. 11 illustrates the saturation profiles obtained by simulation.

The simulated saturation profiles (P01, 02 and P1) are represented to evaluate the extent of the calculation error on the mean saturation in the sample from the resistance measurement. In fact, everything is based on a RI(Sw) calibration. Now, curve RI(Sw) is established from the mean resistance measurement and from the mean saturation in the presence of a saturation profile. Evaluation is desired whether the presence of this saturation profile, whose shape changes depending on the rate of injection, has great significance on the calibration. These profiles, obtained by simulation, are shown in FIG. 11, where L represents the distance to the sample injection face, P01 represents the simulated profile for a flow rate of 0.1 cm³/h, P02 represents the simulated profile for a flow rate of 0.2 cm³/h and P1 represents the simulated profile for a flow rate of 1 cm³/h.

Table 2 hereafter shows the comparison between the mean saturations measured experimentally at the end of each flow rate period and the saturation values obtained by averaging the simulated profile with a system in parallel, that is as seen by the radially arranged electrodes. Therefore, what is measured at a buret at the outlet (total saturation variation) is compared with what the electrical electrodes really measure in the middle of the sample (between the first and the second centimeter). It can be observed that the difference between the two measurements does not exceed 1%, which remains quite acceptable in relation to the calibration precision and which validates the approach selected for evaluating the production volume curve from the resistance measurement.

TABLE 2 evaluation of the pertinence of the resistance curve as a function of the saturation used

| | Experimental Sw | Sw simulated on (1-2 cm) | Error |
|---|---|---|---|
| Injection end at 0.1 cm³/h | 0.66 | 0.658 | −0.2% |
| Injection end at 0.2 cm³/h | 0.695 | 0.69 | −0.5% |
| Injection end at cm³/h | 0.744 | 0.748 | 0.4% |

The invention claimed is:

1. A method for simultaneously evaluating measured electrical resistivity and relative permeability and capillary pressure of a porous medium, from at least one multi-flow type displacement experiment injecting a first injected fluid, into a sample of the medium initially saturated with a second displaced fluid, wherein the injection rate of the injected fluid is increased at least once after a step of stabilization of displaced fluid production volume, comprising:
   continuously measuring, as a function of time, differential pressure between two ends of the sample and an electrical resistivity of the sample;
   measuring for each stabilization step displaced fluid production volume;
   estimating a relation between the electrical resistivity of the sample and the displaced fluid production volume, from the resistivity measurements and the displaced fluid production volume values;
   establishing a continuous curve of the displaced fluid production volume as a function of time, from the relation; and
   estimating the relative permeability and the capillary pressure from the continuous differential pressure measurement and from the continuous curve by a numerical flow simulator.

2. A method as claimed in claim 1, wherein the relation is furthermore estimated from a resistivity curve as a function of a sample saturation at an end of the estimating a relation step.

3. A method as claimed in claim 2, wherein electrodes measuring the electric resistivity are arranged radially around the sample and a sample is used to measure the electrical resistivity.

4. A method as claimed in claim 1, wherein electrodes measuring the electric resistivity are arranged radially around the sample and a sample is used to measure the electrical resistivity.

5. A device for carrying out on a porous solid sample multi-flow displacement experiments, comprising a containment vessel containing the sample saturated with a first displaced fluid, closed at one end by a first cylindrical end part connected to means for injecting under pressure a second injected fluid, and closed at another end by a second cylindrical end part comprising a fluid circulation system, the device also comprising a semi-permeable porous plate between the sample and the first end part, means for continuously measuring the electrical resistivity of the sample, means for measuring a displaced fluid production volume for each stabilization step, and means for continuously measuring between the two ends of the sample a differential pressure of at least one of the fluids.

6. A device as claimed in claim 5, wherein the first cylindrical end part comprises a first cylinder in a second concentric cylinder.

7. A device as claimed in claim 6, wherein the means for continuous measurement of the differential pressure comprises at least one pressure measuring line connected to a differential pressure sensor.

8. A device as claimed in claim 7, wherein the longitudinal slots are machined in an inner surface of the second cylinder.

9. A device as claimed in claim 7, wherein the line comprises longitudinal slots.

10. A device as claimed in claim 9, wherein the longitudinal slots are machined in an outer surface of the first cylinder.

11. A device as claimed in claim 5, wherein the means for continuous measurement of the differential pressure comprises at least one pressure measuring line connected to a differential pressure sensor.

12. A device as claimed in claim 11, comprising a pressure measuring line coupled to the first cylindrical end part for connection to a differential pressure sensor which also prevents coupling of air to the differential pressure sensor.

13. A device as claimed in claim 6, comprising a pressure measuring line coupled to the first cylindrical end part for connection to a differential pressure sensor which also prevents coupling of air to the differential pressure sensor.

* * * * *